(12) United States Patent
Holl et al.

(10) Patent No.: US 9,504,445 B2
(45) Date of Patent: Nov. 29, 2016

(54) ULTRASOUND IMAGING SYSTEM AND METHOD FOR DRIFT COMPENSATION

(71) Applicant: General Electric Company, Schenectady, NY (US)

(72) Inventors: Stefan Holl, Voecklabruck (AT); Stefan Denk, Ried (AT); Thomas Holl, Mondsee (AT); Bernd Arminger, Schwanenstadt (AT)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 197 days.

(21) Appl. No.: 13/780,871

(22) Filed: Feb. 28, 2013

(65) Prior Publication Data

US 2014/0243671 A1    Aug. 28, 2014

(51) Int. Cl.
*A61B 8/00* (2006.01)
*A61B 8/08* (2006.01)

(52) U.S. Cl.
CPC ........... *A61B 8/4254* (2013.01); *A61B 8/4209* (2013.01); *A61B 8/485* (2013.01); *A61B 8/5207* (2013.01); *A61B 8/5276* (2013.01); *A61B 8/58* (2013.01); *A61B 8/4245* (2013.01)

(58) Field of Classification Search
CPC  A61B 8/5253; A61B 8/4245; A61B 8/4254; A61B 8/4263; A61B 8/42; A61B 8/5276; A61B 5/721
USPC .................................................. 600/495, 439
See application file for complete search history.

(56) References Cited

U.S. PATENT DOCUMENTS

| | | | |
|---|---|---|---|
| 6,360,027 B1 * | 3/2002 | Hossack et al. | 382/294 |
| 7,806,824 B2 * | 10/2010 | Ohtake | 600/443 |
| 2003/0105401 A1 * | 6/2003 | Jago et al. | 600/443 |
| 2009/0220125 A1 * | 9/2009 | Ren | A61B 1/00009 382/103 |
| 2012/0029353 A1 * | 2/2012 | Slayton et al. | 600/439 |
| 2014/0128739 A1 * | 5/2014 | Sundaran et al. | 600/459 |

* cited by examiner

*Primary Examiner* — Long V Le
*Assistant Examiner* — Katherine McDonald

(57) ABSTRACT

An ultrasound imaging system and method includes acquiring motion data from a motion sensing system on a probe while acquiring ultrasound data with the probe. The system and method includes acquiring probe motion data with a motion sensing system, acquiring probe position data with a position sensing system and calculating a drift compensation using the probe motion data and the probe position data.

13 Claims, 6 Drawing Sheets

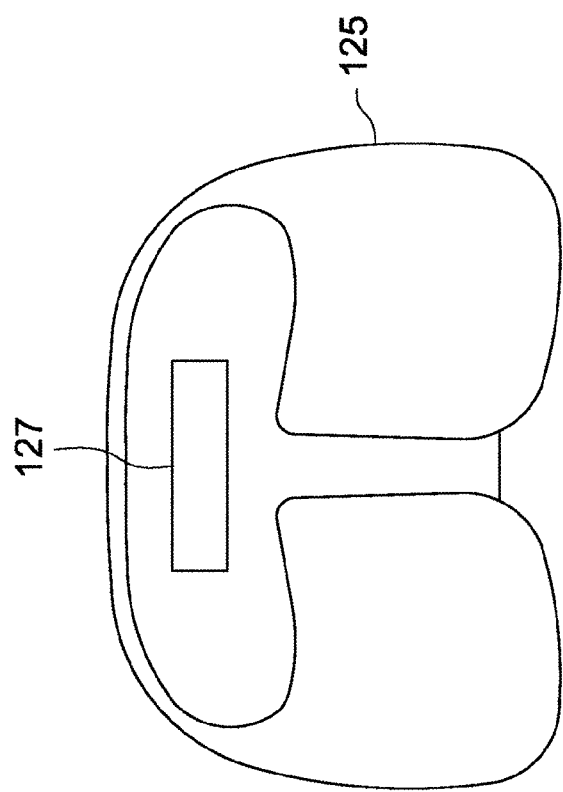

ULTRASOUND IMAGING SYSTEM AND METHOD FOR DRIFT COMPENSATION

FIELD OF THE INVENTION

This disclosure relates generally to an ultrasound imaging system including a probe and a method for applying drift compensation to probe motion data acquired with a motion sensing system attached to the probe.

BACKGROUND OF THE INVENTION

An ultrasound probe equipped with a motion sensor may be used to acquire composite ultrasound data. For example, probe motion data from the motion sensor may be integrated over time in order to calculate the position of the probe at any time. The probe motion data may, therefore, be used to calculate the position of the probe when any of the frames of ultrasound data were acquired. Using the probe position data, two or more of the frames may be combined to generate composite ultrasound data. For example, probe position data for a plurality of frames may be used to generate 3D or 4D ultrasound data of a volume. Or, multiple frames of ultrasound data may be combined to generate a panoramic image. Motion sensors, such as accelerometers and gyro sensors are advantageous to use since they are relatively inexpensive and easy to package into a probe. However, motion sensors are prone to experience drift over time. Drift in the motion sensors may cause error and/or image artifacts in any composite ultrasound data combined based on probe motion data. Therefore, in order for probes with motion sensors to be reliably and accurately used to acquire composite ultrasound data, an improved method and system of ultrasound imaging is desired.

BRIEF DESCRIPTION OF THE INVENTION

The above-mentioned shortcomings, disadvantages and problems are addressed herein which will be understood by reading and understanding the following specification.

In an embodiment, a method of adjusting for drift during ultrasound imaging includes acquiring probe motion data using a motion sensing system, acquiring probe position data using a position sensing system, and calculating a drift compensation using the probe motion data and the probe position data.

In an embodiment, a method of adjusting for motion sensor drift during ultrasound imaging includes removing a probe from a probe holder and acquiring ultrasound data with the probe after removing the probe from the probe holder. The method includes placing the probe back in the probe holder after said acquiring the ultrasound data. The method includes acquiring probe motion data with a motion sensing system attached to the probe during a time period between said removing the probe from the stationary probe holder and placing the probe back in the stationary probe holder. The method also includes calculating a drift compensation based on the probe motion data.

In another embodiment, an ultrasound imaging system includes a probe including at least one transducer element, a motion sensing system attached to the probe, a position sensing system associated with the probe, a display device, and a processor in communication with the probe and the display device. The processor is configured to control the probe to acquire a plurality of frames of ultrasound data, receive probe motion data from the motion sensing system, and receive probe position data from the position sensing system. The processor is configured to detect when the probe is stationary based on the probe position data, and calculate the drift compensation using the probe motion data and the probe position data. The processor is configured to generate composite ultrasound data by combining at least two of the plurality of frames of ultrasound data based on the compensated probe motion data and display an image generated from the composite ultrasound data on the display device.

Various other features, objects, and advantages of the invention will be made apparent to those skilled in the art from the accompanying drawings and detailed description thereof.

BRIEF DESCRIPTION OF THE DRAWINGS

FIG. 6 is a schematic representation of a probe holder in accordance with an embodiment.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
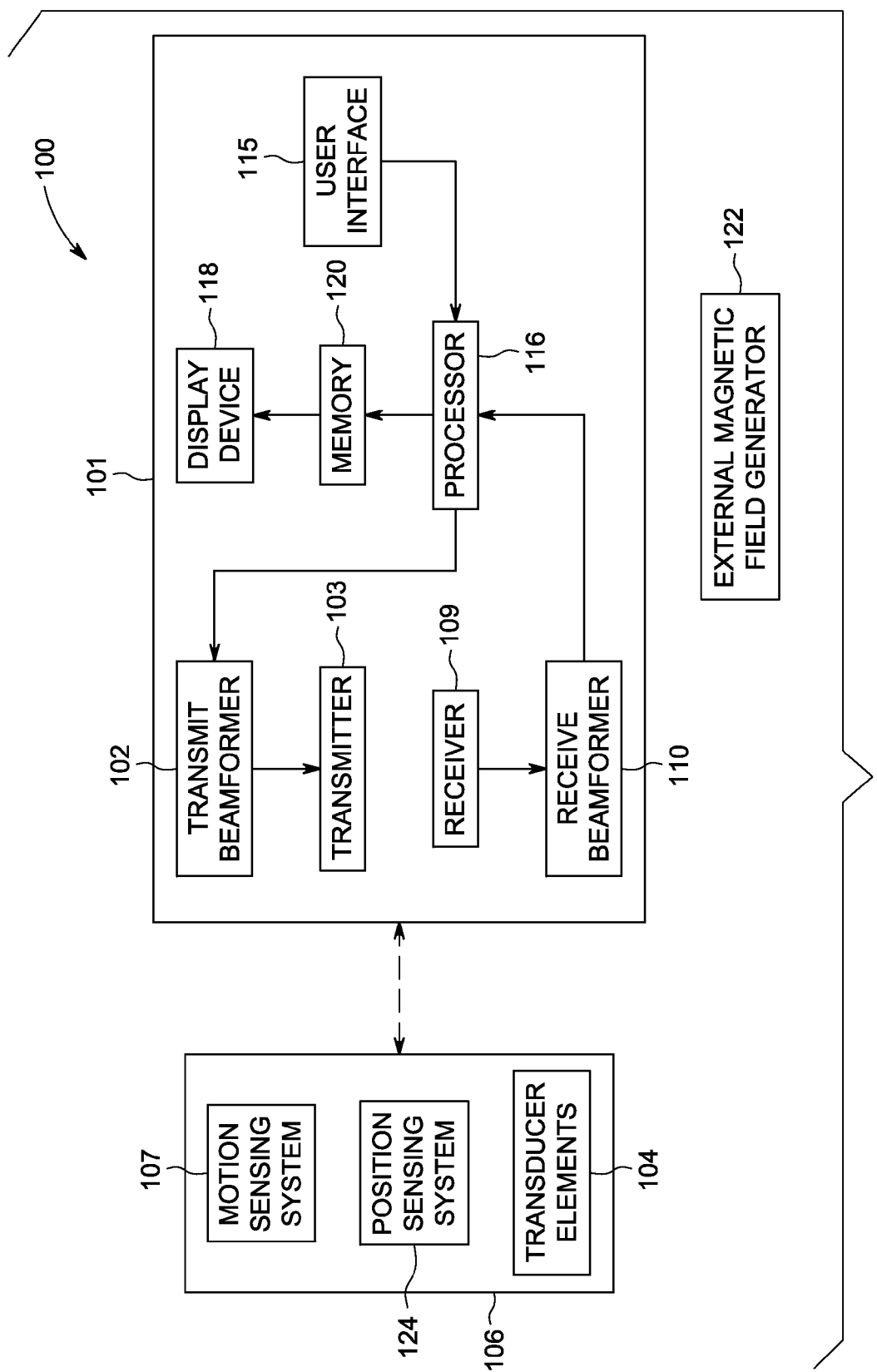
FIG. 1 is a schematic diagram of an ultrasound imaging system in accordance with an embodiment.

FIG. 1 is a schematic diagram of an ultrasound imaging system 100 in accordance with an embodiment. The ultrasound imaging system includes a scan system 101. According to an exemplary embodiment, the scan system 101 may be a hand-held device. For example, the scan system 101 may be similar in size to a smartphone, a personal digital assistant or a tablet. According to other embodiments, the scan system 101 may be configured as a laptop or cart-based system. The ultrasound imaging system 100 includes a transmit beamformer 102 and a transmitter 103 that drive transducer elements 104 within a probe 106 to emit pulsed ultrasonic signals into a body (not shown). The probe 106 includes a motion sensing system 107 in accordance with an embodiment. The motion sensing system 107 may include one or more motion sensors. The motion sensors may be selected from a group including a gyro sensor and an accelerometer. Gyro sensors are configured to detect changes in angular acceleration, while accelerometers are configured to detect changes in linear acceleration. Data collected by the motion sensing system 107 may be used to determine the position of the ultrasound probe 106, preferably in real-time or almost real-time, as a clinician is manipulating the probe 106. According to an exemplary embodiment, the motion sensing system 107 may be a 3-axis motion sensing system including three accelerometers configured to detect acceleration in each of three mutually orthogonal directions and three gyro sensors configured to detect rotational acceleration in any direction. For purposes of this disclosure, the term "real-time" is defined to include an operation or procedure that is performed without any intentional delay. For the purposes of ultrasound imaging, the term "real-time" is defined to include procedures that occur within 500 mS.

The scan system 101 is in communication with the probe 106. The scan system 101 may be physically connected to the probe 106, or the scan system 101 may be in communication with the probe 106 via a wireless communication technique. Still referring to FIG. 1, the pulsed ultrasonic signals are back-scattered from structures in the body, like blood cells or muscular tissue, to produce echoes that return to the elements 104. The echoes are converted into electrical signals, or ultrasound data, by the elements 104 and the electrical signals are received by a receiver 109. The electrical signals representing the received echoes are passed through a receive beamformer 110 that outputs ultrasound data. According to some embodiments, the probe 106 may contain electronic circuitry to do all or part of the transmit and/or the receive beamforming. For example, all or part of the transmit beamformer 102, the transmitter 103, the receiver 109 and the receive beamformer 110 may be situated within the probe 106. The terms "scan" or "scanning" may also be used in this disclosure to refer to acquiring data through the process of transmitting and receiving ultrasonic signals. The term "ultrasound data" may be used in this disclosure to refer to either one or more datasets acquired with an ultrasound imaging system. A user interface 115 may be used to control operation of the ultrasound imaging system 100, including, to control the input of patient data, to change a scanning or display parameter, and the like. The user interface 115 may include one or more of the following: a rotary knob, a keyboard, a mouse, a trackball, a track pad, a touch screen, or any other input device.

The ultrasound imaging system 100 also includes a processor 116 to control the transmit beamformer 102, the transmitter 103, the receiver 109 and the receive beamformer 110. The processor 116 is in communication with the probe 106. The processor 116 may control the probe 106 to acquire ultrasound data. The processor 116 controls which of the elements 104 are active and the shape of a beam emitted from the probe 106. The processor 116 is also in communication with a display device 118, and the processor 116 may process the data into images for display on the display device 118. According to other embodiments, part or all of the display device 118 may be used as the user interface. For example, some or all of the display device 118 may be enabled as a touch screen or a multi-touch screen. For purposes of this disclosure, the phrase "in communication" may be defined to include both wired and wireless connections. The processor 116 may include a central processor (CPU) according to an embodiment. According to other embodiments, the processor 116 may include other electronic components capable of carrying out processing functions, such as a digital signal processor, a field-programmable gate array (FPGA) or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the RF data and generates raw data. In another embodiment the demodulation can be carried out earlier in the processing chain. The processor 116 may be adapted to perform one or more processing operations according to a plurality of selectable ultrasound modalities on the data. The data may be processed in real-time during a scanning session as the echo signals are received. Some embodiments of the invention may include multiple processors (not shown) to handle the processing tasks. For example, a first processor may be utilized to demodulate and decimate the RF signal while a second processor may be used to further process the data prior to displaying an image. It should be appreciated that other embodiments may use a different arrangement of processors.

The ultrasound imaging system 100 may continuously acquire data at a rate of, for example, 10 Hz to 50 Hz. Images generated from the data may be refreshed at a similar rate. Other embodiments may acquire and display data at different rates. A memory 120 is included for storing frames of acquired data. In an exemplary embodiment, the memory 120 is of sufficient capacity to store at least several seconds worth of frames of ultrasound data. The frames of data are stored in a manner to facilitate retrieval thereof according to its order or time of acquisition. The memory 120 may comprise any known data storage medium. According to an embodiment, the memory 120 may be a ring buffer or circular buffer.

Optionally, embodiments of the present invention may be implemented utilizing contrast agents. Contrast imaging generates enhanced images of anatomical structures and blood flow in a body when using ultrasound contrast agents including microbubbles. After acquiring data while using a contrast agent, the image analysis includes separating harmonic and linear components, enhancing the harmonic component and generating an ultrasound image by utilizing the enhanced harmonic component. Separation of harmonic components from the received signals is performed using suitable filters. The use of contrast agents for ultrasound imaging is well-known by those skilled in the art and will therefore not be described in further detail.

In various embodiments of the present invention, data may be processed by other or different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate and combinations thereof, and the like. The image beams and/or frames are stored and timing information indicating a time at which the data was acquired in memory may be recorded. The modules may include, for example, a scan conversion module to perform scan conversion operations to convert the image frames from coordinate beam space to display space coordinates. A video processor module may be provided that reads the image frames from a memory and displays the image frames in real time while a procedure is being carried out on a patient. A video processor module may store the image frames in an image memory, from which the images are read and displayed.

The ultrasound imaging system 100 also includes a position sensing system 124 attached to the probe 106. The position sensing system 124 may include an optical tracking system, a magnetic position system, a sensor in a probe holder, or any other system configured to detect the position of the probe 106 through a different technique than the motion sensing system 107. The ultrasound imaging system 100 may also include an external magnetic field generator 122. The external magnetic field generator 122 may include a coil, a permanent magnet, or a combination of a coil and a permanent magnet. When energized with electrical current, the coil may generate an external magnetic field. The external magnetic field may be static according to an exemplary embodiment. The position sensing system 124 may be configured to detect a preexisting magnetic field or the magnetic field generated by the external magnetic field generator 122. The external magnetic field generator 122 may be configured to generate a magnetic field with a gradient so that the position of the magnetic position sensor may be determined based on the detected magnetic field.

Figure 2:
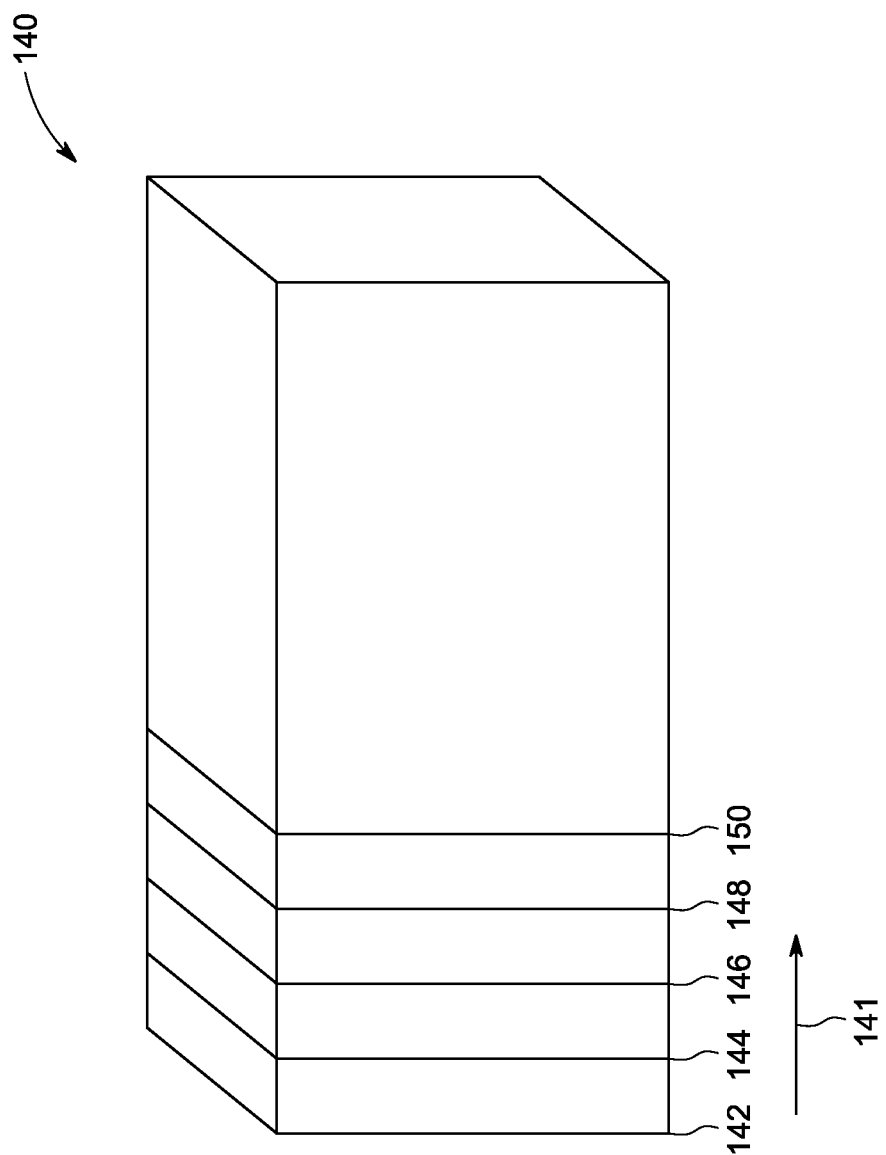
FIG. 2 is a schematic representation of an acquisition pattern in accordance with an embodiment.

FIG. 2 is a schematic representation of an acquisition pattern 140 that may be performed with the probe 106 (shown in FIG. 1) in order to acquire 3D ultrasound data of a volume. In the acquisition pattern 140, a probe, such as the probe 106, may be translated in a direction 141. While the probe 106 is translated, frames of ultrasound data are acquired. For example, frame 142 is acquired from a first location, frame 144 is acquired from a second location, frame 146 is acquired from a third location, frame 148 is acquired from a fourth location, and frame 150 is acquired from a fifth location. While only five frames are schematically represented on FIG. 2, it should be appreciated that any number of frames of ultrasound data may be acquired according to the acquisition pattern 140. The acquisition pattern shown in FIG. 2 is just one exemplary embodiment and it should be appreciated that other acquisition patterns may be used to acquire 3D ultrasound data using the motion sensing system of the ultrasound imaging system 100. A non-limiting list of additional acquisition patterns that may be used to acquire 3D or 4D ultrasound data includes rotating the probe 106 about an axis, sweeping the probe through an angle, and freehand scanning of a volume.

Figure 3:
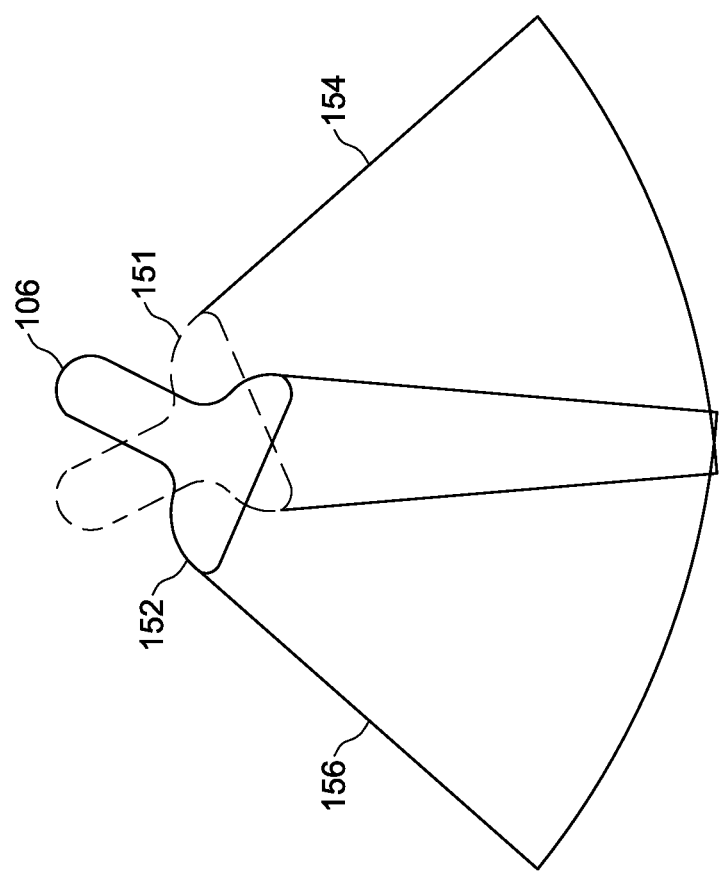
FIG. 3 is a schematic representation of an acquisition pattern in accordance with an embodiment.

FIG. 3 is a schematic representation of an acquisition pattern that may be used to acquire a panoramic image. The acquisition pattern involves tilting the probe 106 in a direction generally parallel to the imaging plane. In the embodiment shown in FIG. 3, the probe 106 is tilted from a first position 151 to a second position 152. The first position 150 of the probe 106 is indicated by the dashed line. In the process of tilting the probe 106, a first frame of data 154 is acquired from the first position 150 and a second frame of data 156 is acquired from the second or final position 152. By using probe motion data acquired with the motion sensing system 107, the processor 116 may combine the first frame of ultrasound data 154 with the second frame of ultrasound data 156 to create a panoramic image with a wider field of view since the first frame of data 154 and the second frame of data 156 are generally coplanar. For purposes of this disclosure, the term "panoramic image" includes an image acquired from two or more different probe locations and including a wider field-of-view. According to other embodiments, panoramic data may be acquired by translating the probe 106 in a direction generally parallel to the imaging plane.

Figure 4:
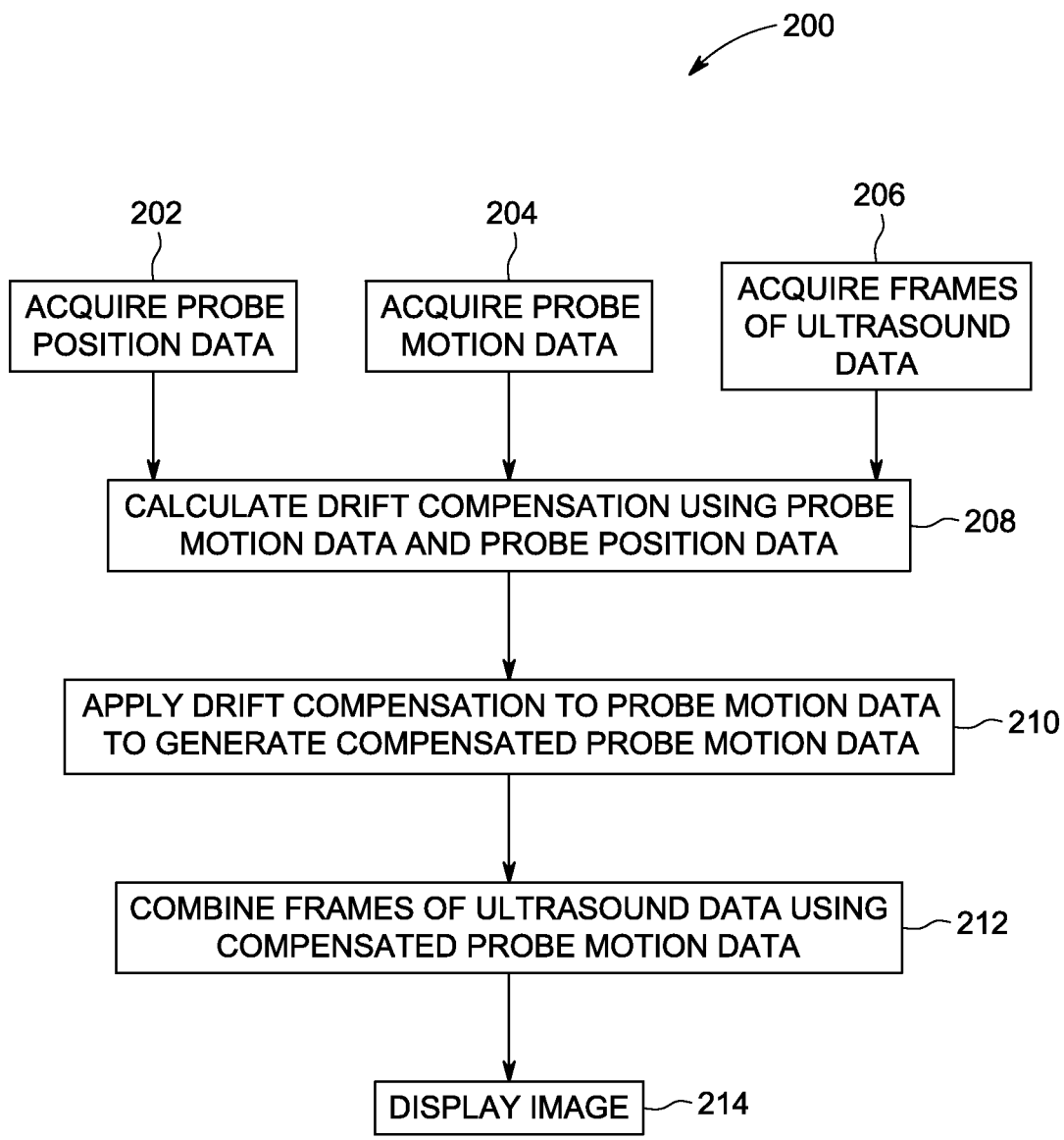
FIG. 4 is a flow chart in accordance with an embodiment.

FIG. 4 is a flow chart of a method in accordance with an exemplary embodiment. The individual blocks of the flow chart represent steps that may be performed in accordance with the method 200. Additional embodiments may perform the steps shown in a different sequence and/or additional embodiments may include additional steps not shown in FIG. 4. The technical effect of the method 200 is the calculation of a drift compensation using both probe motion data and probe position data. The method 200 will be described according to an exemplary embodiment where the method 200 is implemented by the processor 116 of the ultrasound imaging system 100 of FIG. 1.

Referring to FIGS. 1 and 4, at step 202, the position sensing system 124 acquires probe position data. According to an embodiment, the position sensing system 124 may be a magnetic position sensing system and the probe position data indicates the position of the probe 106 within a magnetic field. At step 204, the motion sensing system 107 acquires probe motion data. According to an exemplary embodiment, the motion sensing system 107 is a 3-axis motion sensing system including three accelerometers and three gyro sensors. The motion sensing system 107 may be configured to detect both linear accelerations of the probe 106 in any direction and rotational accelerations about multiple axes through the probe 106. At step 206, the processor 116 controls the transmit beamformer 102, the transmitter 103, and the probe 106 to acquire a plurality of frames of ultrasound data. A clinician may be moving the probe 106 while acquiring some of all the frames of ultrasound data.

According to an exemplary embodiment, steps 202, 204 and 206 may all be performed in parallel. For example, the position sensing system 124 and the motion sensing system 107 may both be configured to acquire probe position data and probe motion data continuously at regularly sampled intervals. A clinician may be maneuvering the probe 106 while acquiring the frames of ultrasound data at step 206. At the same time as the clinician is acquiring the frames of ultrasound data, probe position data may be acquired with the position sensing system 124 (step 202) and probe motion data may be acquired from the motion sensing system 107 (step 204). According to an embodiment, the probe position data and/or the probe motion data may be acquired during times when the probe 106 is stationary as well.

The clinician may manipulate the probe 106 in order to acquire composite ultrasound data. For purposes of this disclosure, the term "composite ultrasound data" is defined to include ultrasound data that is generated by combining two or more individually acquired frames of ultrasound data. Composite ultrasound data may include a larger field of view than a single frame of data, such as is the case when generating a panoramic image. An example of an acquisition pattern that could be used to acquire a panoramic image is shown in FIG. 3. Composite ultrasound data may also include a plurality of frames acquired from different locations used to acquire a 3D or 4D ultrasound dataset. The acquisition pattern shown in FIG. 2 is one example of an acquisition pattern that could be used to acquire 3D or 4D ultrasound data.

According to an embodiment where the position sensing system 124 is a magnetic positioning system, the probe position data tends to be accurate, but with a low level of precision. The position sensing system 124 is therefore very useful for determining whether or not the probe 106 is moving or stationary. In contrast, the motion sensing system 107 may include a combination of gyro sensors and accelerometers that can detect accelerations with a relatively high level of precision. As previously described, accelerometers are configured for detecting linear accelerations while gyro sensors are configured for detecting rotational accelerations. By integrating signals acquired by each accelerometer or gyro sensor over time, the processor 116, or a separate processor (not shown) may use the probe motion data acquired by the motion sensing system 107 to calculate the position and orientation of the probe 106. In order to calculate probe position based on probe motion data, the initial position of the probe 106 must be known. If the initial position is not known, probe motion data may be used to calculate the relative position of the probe 106, and therefore each of the frames, while acquiring ultrasound data. Off-the-shelf accelerometers and gyro sensors are available that provide very precise acceleration data. Calculating probe position based on data from the motion sensing system 107, therefore, allows for more precise position information than relying only on probe position data acquired from the position sensing system 124.

As discussed previously, one limitation of calculating probe 106 position based on probe position data acquired with the motion sensing system 107 is that motion sensors, such as accelerometers and gyro sensors are prone to experiencing drift. Drift is defined to include a low frequency change in the sensor over time. Drift may result in the change of a baseline, or zero value, of a particular motion sensor over time. Motion sensor drift introduces an error into measurements performed with a particular motion sensor unless an appropriate correction is applied. At step 208, the processor 116 calculates a drift compensation for the probe motion data using both the probe motion data and the probe position data. The drift compensation may be calculated in different ways according to various embodiments.

Figure 5:
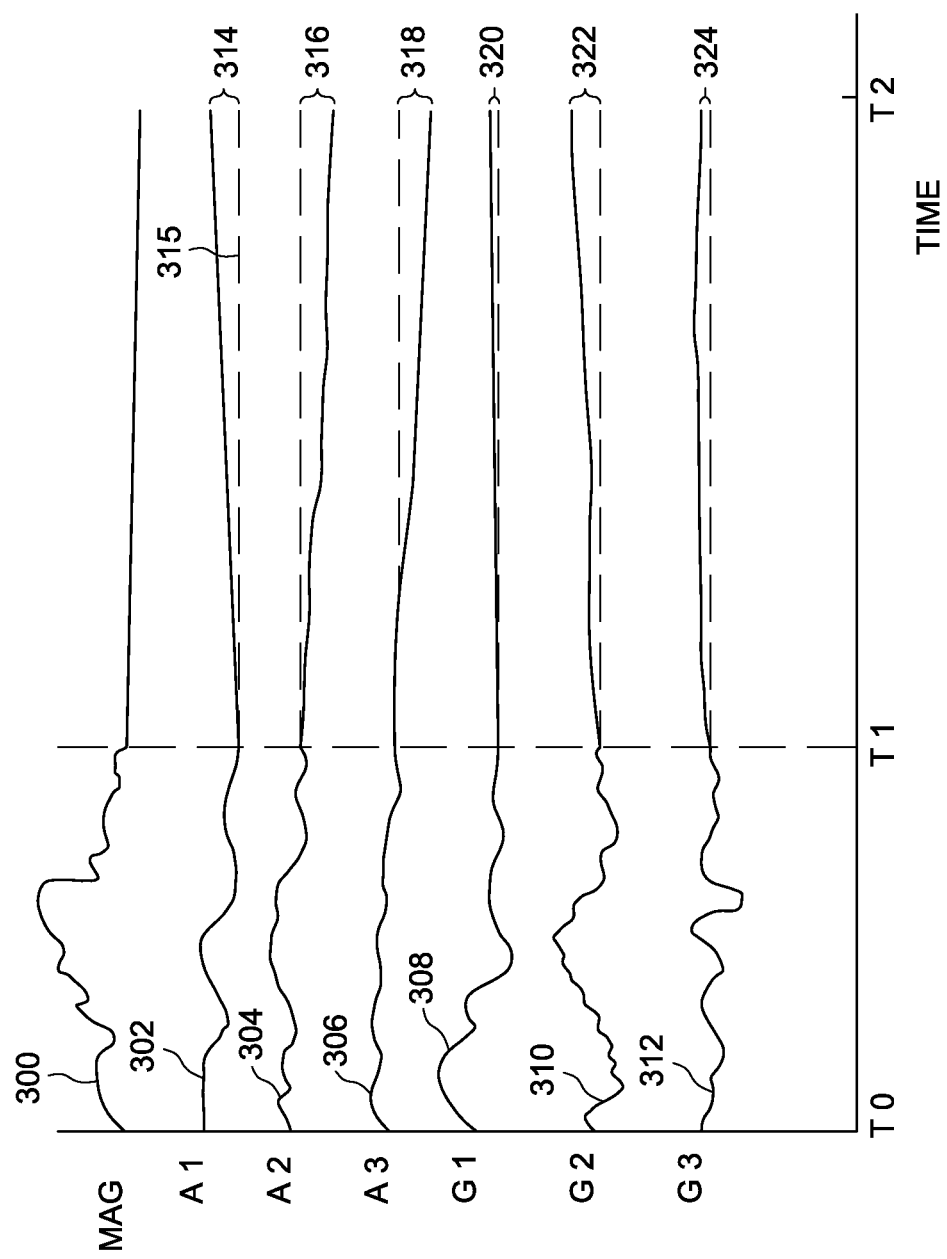
FIG. 5 is a graph showing probe position data and probe motion data in accordance with an embodiment.

FIG. 5 is a graph showing traces representing data acquired by a magnetic position sensor, and six motion sensors in accordance with an exemplary embodiment. Trace 300 represents data acquired with a magnetic position sensor that is included in the position sensing system 124. Trace 302, trace 304, trace 306, trace 308, trace 310, and trace 312 are all acquired by the motion sensing system 107. Traces 302, 304, and 306 represent probe motion data acquired with different accelerometers, while traces 308, 310, and 312 represent probe motion data acquired with different gyro sensors. From time T0 until time T1, trace 300 shows significant movement. Likewise, traces 302, 304, 306, 308, 310, and 312 also show significant movement. Trace 300 represents probe position data, and the probe position data from time T0 until time T1 indicates that the probe 106 is in motion. Traces 302, 304, 306, 308, 310, and 312 all represent probe motion data, or acceleration. The non-zero values represented in traces 302, 304, 306, 308, 310, and 312 from time T0 until T1 are consistent with the motion indicated in trace 300. However, after time T1, trace 300 shows no movement, indicating that the probe 106 is stationary. However, note that the slopes of the traces representing probe motion data, i.e. traces 302, 304, 306, 308, 310, and 312, are not flat. Uncorrected, the data from the time T1 until T2 would indicate that the probe 106 is being moved since the probe motion data is not zero. The processor 116 is adapted to detect that the probe motion data contains drift based on the probe position data acquired by the position sensing system 124.

According to an embodiment, the processor 116 may detect that the probe 106 is stationary based on the probe position data, such as that acquired by a magnetic positioning system. Based on the position data represented by the trace 300, this would correspond to the time period between T1 and T2. Next, the processor 116 may analyze the probe motion data from the time while the probe 106 is stationary to determine an amount of drift in the motion sensing system 107 and an appropriate drift compensation. FIG. 5 shows an exemplary embodiment where the motion sensing system comprises 6 individual motion sensors. The drift compensation may, therefore, include an individual compensation for each of the six motion sensors. That is, the processor 116 may calculate an individual drift compensation for each of the accelerometers and each of the gyro sensors. For purposes of this disclosure, the term "drift compensation" may either apply collectively to a plurality of adjustments applied to probe motion data acquired with multiple motion sensors, or "drift compensation" may apply to the adjustment applied to probe motion data acquired with a single motion sensor.

Referring to FIG. 5, trace 302 shows a positive drift of an amount 314 from the time period from T1 to T2. The baseline, or zero value, for each of the traces is shown by a dashed line, such as dashed line 315. Trace 304 shows a negative drift of an amount 316, trace 306 shows a negative drift of an amount 318, trace 308 shows a positive drift of an amount 320, trace 310 shows a positive drift of an amount 322, and trace 312 shows a positive drift of an amount 324. All of the probe motion data shown in FIG. 5 exhibits zero offset at the time T1.

The processor 116 may determine the amount of drift in the probe motion data acquired from each of the motion sensors. The processor 116 may then calculate a drift compensation. According to an embodiment, the drift compensation may include a linear adjustment to the probe motion data based on time of acquisition. According to another embodiment, the drift compensation may include an exponential adjustment to the probe motion data based on time of acquisition. According to another embodiment, the drift compensation may include a best fit function based on a time of acquisition. According to other embodiments, the drift compensation may include a fixed offset or adjustment to the probe motion data.

The following embodiment will be described using a linear adjustment to the probe motion data based on time. It should be appreciated that any other type of best fit function, including a polynomial function or an exponential function may be used in other embodiments. According to an exemplary embodiment, the processor 116 may detect the amount of drift in the probe motion data from each of the motion sensors while the probe 106 is stationary. As was described previously, without drift, the motion sensors should record probe motion data indicating zero probe motion while the probe 106 is stationary. Any non-zero measurements in the probe motion data between time T1 and T2 would be caused by drift since the probe 106 remained stationary between T1 and T2 as indicated by the probe position data in trace 300.

For example, trace 302 shows a positive drift of amount 314 from time T1 to time T2. The processor 116 may model the drift by fitting probe motion data from each motion sensor to a function, such as a line according to an exemplary embodiment. The line would represent the rate of drift of the motion sensor over time. The line or other function that models the behavior of the motion sensor represents the drift over a period of time. The drift compensation, as calculated by the processor, includes data generated by subtracting or otherwise removing an estimated amount of drift from probe motion data acquired by the motion sensing system 107. The estimated amount of drift may be calculated based on the function used to model the drift as will be described in detail hereinafter. The processor 116 may model the drift of each motion sensor according to an individual function. The function for each motion sensor may be a function with a predetermined relationship, or the function may be a best fit function that provides the highest correlation to the data acquired while the probe 106 is stationary. According to one embodiment, the processor 116 may calculate unique drift compensations for each of the six motion sensors shown in FIG. 5.

At step 210, the processor 116 applies the drift compensation to the probe motion data to generate compensated probe motion data. As previously described, drift compensation was calculated for each of the motion sensors in the motion sensing system 107. At step 210, the processor adjusts the probe motion data based on the drift compensation. According to an embodiment where the drift compensation includes a linear adjustment based on time, the processor 116 then applies the drift compensation to the probe motion data. According to an embodiment, the motion sensors in the motion sensing system 107 may be zeroed, or reset to a baseline of zero, when the probe is turned on or removed from a probe holder. The motion sensing system 107 may be zeroed automatically based on feedback from the position sensing system 124. For example, the motion sensing system 107 may be automatically zeroed every time the probe 106 is stationary for a long enough period of time, or the motion sensing system 107 may be manually zeroed in response to a user command. The processor 116 may apply the drift compensation to the probe motion data either retrospectively or prospectively. In other words, the processor 116 may apply the drift compensation to probe motion data that was acquired before the drift compensation was calculated, or the processor 116 may apply the drift compensation to probe motion data acquired after the drift compensation was calculated.

The processor 116 may apply the drift compensation to the probe motion data starting from a time when the motion sensing system 107 was zeroed. According to an embodiment, the correction applied to the probe motion data may depend upon the time that the data was acquired. For example, the processor 116 may use the function that was fit to the drift data to calculate the drift compensation that needs to be applied to the probe motion data acquired from each specific motion sensor. The processor 116 may use time from the last time the motion sensing system 107 was zeroed as an input into the function describing the drift of a particular motion sensor. The function may then be used to estimate the motion sensor drift at any particular time after the motion sensing system 107 was zeroed. In order to apply the drift compensation, the processor 116 may remove or subtract the amount of drift as estimated by the function of functions modeling the drift of the motion sensing system 107.

According to another embodiment, the processor 116 may calculate and apply the drift compensation during steps 208 and 210 according to an alternative technique. The processor 116 may still fit the motion data to a function based on the period of time when the probe 106 is not moving. Drift compensation may be calculated by extrapolating the function. For example, if probe motion data was acquired before calculating the drift compensation, the function may be extrapolated to compensate the probe motion data acquired during the period of time before the probe 106 was stationary. Additionally, if the probe motion data was acquired after calculating the drift compensation, the function may be extrapolated to compensate the probe motion data that was acquired after the probe 106 was stationary. Therefore, the function modeling the drift while the probe 106 was stationary may be extrapolated in either direction.

The ultrasound imaging system 100 may optionally include a probe holder adapted to receive or retain the probe 106. FIG. 6 is a schematic representation of a probe holder 125 in accordance with an embodiment. The probe holder 125 is adapted to receive a portion of the probe 106, such as the handle. The probe holder 125 may be constructed from a flexible material, to make it easier for the user to place the probe 106 in the probe holder 125 or remove the probe 106 from the probe holder 125. The probe holder 125 may be attached to a portion of the ultrasound imaging system 100 that is stationary while acquiring ultrasound data. For example, if the ultrasound imaging system 100 is a cart-based system, the probe holder 125 may be attached to the cart. If the ultrasound imaging system 100 is a laptop based system, the probe holder 125 may be attached to the laptop. The probe holder 125 includes a sensor 127 that is adapted to detect when the probe 106 is placed in the probe holder and communicate with the processor 116. The sensor 127 may be any type of sensor, including a capacitive sensor, an infrared sensor, or a pressure sensor.

Since the position of the probe holder 125 is fixed during an ultrasound exam, probe position data acquired from the sensor 127 may be used to help adjust for drift. The probe position data may include data communicating whether or not the probe 106 is positioned in the probe holder 125. According to an exemplary embodiment, the processor 116 may automatically zero the motion sensors in the motion sensing system 107 each time that the sensor 127 detects that the probe 106 is in the probe holder 125, and therefore stationary. This helps to ensure that the motion sensors have a minimal amount of drift due to being zeroed each time the probe 106 is placed in the probe holder 125. According to another embodiment, a user may remove the probe 106 from the probe holder 125, acquire ultrasound data with the probe 106, and then return the probe 106 back to the probe holder 125. The processor 116 may compare first probe motion data acquired from the motion sensing system 107 while the probe 106 is in the probe holder 125 before acquiring the ultrasound data with second probe motion data acquired from the motion sensing system 107 while the probe 106 is in the probe holder 125 after acquiring the ultrasound data. Since the probe holder 125 is stationary, the first probe motion data should be the same as the second probe motion data. Any difference detected between the first probe motion data and the second probe motion data would be caused by drift within the motion sensing system 107. According to an embodiment, the processor 116 may compare the first probe motion data to the second probe motion data. If the difference between the first probe motion data and the second probe motion data is within a predetermined threshold, the processor 116 may give an indication that the ultrasound data is acceptable in terms of drift or simply display an image based on the ultrasound data. If the difference between the first probe motion data and the second probe motion data is greater than the predetermined threshold, the processor 116 may give a warning that the level of drift in the motion sensing system 107 is unacceptable. The warning may be communicated as an audible warning, or a visible warning on the display device 118.

According to another embodiment, the processor 116 may use the first probe motion data (collected while the probe 106 was placed in the probe holder 125 before the acquisition of the ultrasound data) and the second probe motion data (collected while the probe 106 was placed in the probe holder 125 after the acquisition of the ultrasound data) to calculate a drift compensation. Since the probe 106 is stationary while in the probe holder 125, both the first probe motion data and the second probe motion data should be zero while the probe 106 is in the probe holder 125. Any difference between the first probe motion data and the second probe motion data may be attributable to drift of the motion sensing system 107. A function of drift versus time may be fit to the first probe motion data and the second probe motion data. This function, in turn, may be used to determine a drift compensation for any additional probe motion data acquired during the acquisition of the ultrasound data.

At step 212, the processor 116 combines two or more of the plurality of frames of ultrasound data using the compensated probe motion data. Since the compensated probe motion data has been corrected for drift intrinsic to the motion sensing system 107, the compensated motion data should accurately reflect the motion of the probe 106 regarding both linear and rotational accelerations. The processor 116 may then integrate the compensated motion data over time in order to calculate the position of the probe 106 at any time. Integrating compensated probe motion data provides an accurate and precise way to determine the position of the probe. The processor 116 may calculate the position of the probe 106 at the time when each frame of ultrasound data was acquired and, therefore, also calculate the position of each frame of ultrasound data. For many ultrasound operations, it is not necessary to know the absolute position of the probe 106. Instead, it is typically sufficient to calculate the relative position of the probe 106 when acquiring the plurality of frames of ultrasound data. According to an embodiment, the processor 116 may associate probe position data with each frame of ultrasound data, such as by using a time stamp, or by associating the ultrasound data with the probe position data in a memory or buffer.

Still referring to step 212, the processor 116 may combine two or more frames of ultrasound data to generate composite ultrasound data. The term "composite ultrasound data" is defined to include ultrasound data generated by combining two or more frames of ultrasound data that were acquired at different spatial locations. For example, the processor 116 may combine two or more frames of ultrasound data into panoramic data. The processor 116 may use compensated probe position data associated with each frame of ultrasound data in order to generate the panoramic data. Data defining the relative position of each of the frames of ultrasound data may be determined based on the compensated probe position data and the parameters used to acquire the frames of ultrasound data.

The processor 116 may also combine a plurality of the frames of ultrasound data to form three-dimensional (3D) or four-dimensional (4D) ultrasound data. Three-dimensional ultrasound data may be generated by combining a plurality of frames of ultrasound data that were acquired from within a volume by moving the probe 106. As described previously, the plurality of frames of ultrasound data may be acquired by probe motion patterns including translating the probe 106, rocking the probe 106, and rotating the probe, as well as other freehand patterns of moving the probe 106. The processor 116 may calculate the probe position by integrating the compensated probe motion data over time.

At step 214, the processor 116 displays an image based on the composite ultrasound data on the display device 118. If the composite ultrasound data includes panoramic data, the image may be a panoramic image. However, if the composite ultrasound data includes 3D or 4D ultrasound data, the image may include a rendering of the composite ultrasound data, a 2D image of a slice plane through the composite data, or any other type of image generated from a 3D or 4D set of ultrasound data.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A method of adjusting for motion sensor drift during ultrasound imaging with an ultrasound imaging system, the ultrasound imaging system comprising:
   a probe including at least one transducer element;
   a motion sensing system attached to the probe, the motion sensing system comprising an accelerometer or a gyro sensor;
   a position sensing system associated with the probe, where the position sensing system is different from the motion sensing system;
   a display device; and
   a processor in communication with the probe and the display device, the method comprising:
      controlling the probe with the processor to acquire a plurality of frames of ultrasound data;
      acquiring probe motion data with the motion sensing system during the process of controlling the probe with the processor to acquire the plurality of frames of ultrasound data;
      receiving, with the processor, probe motion data from the motion sensing system;
      receiving, with the processor, probe position data from the position sensing system;
      detecting, with the processor, when the probe is stationary based on the probe position data;
      calculating, with the processor, a drift compensation for the probe motion data using the probe motion data and the probe position data, where the drift compensation comprises an adjustment to compensate for an amount of drift in the motion sensing system;
      applying the drift compensation to the probe motion data to generate compensated probe motion data;
      generating, with the processor, composite ultrasound data by combining at least two of the plurality of frames of ultrasound data based on the compensated probe motion data; and
      displaying an image generated from the composite ultrasound data on the display device.

2. The method of claim 1, wherein the position sensing system is selected from an optical tracking system, a magnetic position system, and a sensor in a probe holder.

3. The method of claim 1, wherein the motion sensing system comprises an accelerometer and a gyro sensor.

4. The method of claim 1 wherein acquiring the plurality of frames is performed before said calculating the drift compensation.

5. The method of claim 1, wherein acquiring the plurality of frames is performed after said calculating the drift compensation.

6. The method of claim 1, wherein said calculating the drift compensation is performed based on probe motion data acquired while the probe is stationary.

7. The method of claim 1, wherein said calculating the drift compensation is performed based on probe motion data acquired while the probe is moving.

8. An ultrasound imaging system comprising:
   a probe including at least one transducer element;
   a motion sensing system attached to the probe, the motion sensing system comprising an accelerometer or a gyro sensor;
   a position sensing system associated with the probe, where the position sensing system is different from the motion sensing system;

a display device; and a processor in communication with the probe and the display device, wherein the processor is configured to:
  control the probe to acquire a plurality of frames of ultrasound data;
  receive probe motion data from the motion sensing system;
  receive probe position data from the position sensing system;
  detect when the probe is stationary based on the probe position data;
  calculate a drift compensation for the probe motion data using the probe motion data and the probe position data, where the drift compensation comprises an adjustment to compensate for an amount of drift in the motion sensing system;
  apply the drift compensation to the probe motion data to generate compensated probe motion data;
  generate composite ultrasound data by combining at least two of the plurality of frames of ultrasound data based on the compensated probe motion data; and
  display an image generated from the composite ultrasound data on the display device.

9. The ultrasound imaging system of claim 8, wherein the position sensing system comprises a magnetic position sensor attached to the probe.

10. The ultrasound imaging system of claim 9, wherein the position sensing system further comprises an external magnetic field generator configured to emit a magnetic field detectable by the magnetic position sensor.

11. The ultrasound imaging system of claim 8, further comprising a probe holder, and wherein the position sensing system comprises a sensor attached to the probe holder.

12. The ultrasound imaging system of claim 11, wherein the processor is configured to detect that the probe is stationary by detecting that it has been placed in the probe holder.

13. The ultrasound imaging system of claim 8, wherein the drift compensation is selected from the group consisting of a linear adjustment to the motion data based on a time of acquisition, an exponential adjustment to the motion data based on a time of acquisition, and a best fit function based on a time of acquisition.

* * * * *